(12) United States Patent
Zhao et al.

(10) Patent No.: US 12,419,951 B2
(45) Date of Patent: Sep. 23, 2025

(54) PREPARATION OF ZINC RISEDRONATE MICRO/NANO ADJUVANT AND USE THEREOF AS VACCINE ADJUVANT

(71) Applicants: XIAMEN UNIVERSITY, Fujian (CN); XIAMEN INNOVAX BIOTECH CO., LTD., Fujian (CN)

(72) Inventors: Qinjian Zhao, Fujian (CN); Xiaofen Huang, Fujian (CN); Yike Li, Fujian (CN); Meifeng Nie, Fujian (CN); Siyi Chen, Fujian (CN); Ningshao Xia, Fujian (CN)

(73) Assignees: Xiamen University, Fujian (CN); Xiamen Innovax Biotech Co., Ltd., Fujian (CN)

( * ) Notice: Subject to any disclaimer, the term of this patent is extended or adjusted under 35 U.S.C. 154(b) by 896 days.

(21) Appl. No.: 17/615,493

(22) PCT Filed: Mar. 31, 2020

(86) PCT No.: PCT/CN2020/082443
§ 371 (c)(1),
(2) Date: Nov. 30, 2021

(87) PCT Pub. No.: WO2020/238394
PCT Pub. Date: Dec. 3, 2020

(65) Prior Publication Data
US 2022/0233687 A1    Jul. 28, 2022

(30) Foreign Application Priority Data
May 30, 2019 (CN) .......................... 201910459715.6

(51) Int. Cl.
| A61K 39/29 | (2006.01) |
| A61K 39/25 | (2006.01) |
| A61K 39/39 | (2006.01) |
| A61P 31/22 | (2006.01) |
| A61P 37/04 | (2006.01) |
| A61K 39/00 | (2006.01) |

(52) U.S. Cl.
CPC ............. *A61K 39/39* (2013.01); *A61K 39/25* (2013.01); *A61P 31/22* (2018.01); *A61P 37/04* (2018.01); *A61K 2039/55511* (2013.01); *A61K 2039/55516* (2013.01)

(58) Field of Classification Search
None
See application file for complete search history.

(56) References Cited

U.S. PATENT DOCUMENTS

| 8,445,718 | B2 | 5/2013 | Suwa et al. |
| 9,573,811 | B2 | 2/2017 | Thiriot |
| 9,649,372 | B2 | 5/2017 | Harper et al. |
| 10,471,141 | B2 | 11/2019 | Shishido et al. |
| 10,925,936 | B2* | 2/2021 | Shishido ............... A61K 31/415 |
| 2011/0034418 | A1 | 2/2011 | Beltz et al. |
| 2017/0281759 | A1 | 10/2017 | Shishido et al. |
| 2019/0321465 | A1 | 10/2019 | Zhang et al. |
| 2020/0254089 | A1 | 8/2020 | Asari et al. |
| 2022/0193231 | A1* | 6/2022 | Zhao ...................... A61K 39/12 |
| 2024/0000813 | A1* | 1/2024 | Zhao ...................... A61K 39/12 |

FOREIGN PATENT DOCUMENTS

| CN | 101972477 A | 2/2011 |
| CN | 102046152 A | 5/2011 |
| CN | 102421785 A | 4/2012 |
| CN | 102939105 A | 2/2013 |
| CN | 103768595 B | 3/2016 |
| CN | 105669838 A | 6/2016 |
| CN | 106687127 A | 5/2017 |
| CN | 106687138 A | 5/2017 |
| CN | 108289902 A | 7/2018 |
| CN | 110665000 A | 1/2020 |
| DE | 4244422 A1 | 12/1992 |
| WO | 2018/225784 A1 | 12/2018 |

OTHER PUBLICATIONS

Kharuja et al. (Materials Science and Engineering, 2016, p. 78-87).*
English Abstract of Lin et al., "Application and Mechanism of Calcium Phosphate Nanoparticles as Vaccine Adjuvant," Chinese Master's Theses Full-Text Database, Medicine & Health Sciences. Published Jul. 21, 2019.
Tonti et al., "Bisphosphonates Target B Cells to Enhance Humoral Immune Responses," Cell Reports 5:323-330 (2013).
Xia et al., "The Mevalonate Pathway Is a Druggable Target for Vaccine Adjuvant Discovery," Cell 175:1059-1073 (2018).
English translation of the International Search Report in PCT/CN2020/082443, mailed Jun. 28, 2020.
Ai et al., "Analysis of physicochemical properties of three aluminum hydroxide adjuvant," Chinese Journal of Biologicals 28(1):44-47 (2015).
Gao et al., "The Role of Zinc and Zinc Homeostasis in Macrophage Function," Journal of Immunological Research 2018:6872621 (2018).
Goldenthal et al., "Safety evaluation of vaccine adjuvants: National Cooperative Vaccine Development Working Group," AIDS Res Hum Retroviruses 9(1):S47-S51 (1993).

(Continued)

*Primary Examiner* — Agnieszka Boesen
(74) *Attorney, Agent, or Firm* — MEDLER FERRO WOODHOUSE & MILLS PLLC (57) ABSTRACT

The present invention pertains to the field of pharmaceutical technology. Specifically, the present invention relates to a zinc risedronate micro/nano adjuvant with sustained-release function formed by mineralization of zinc ions and risedronic acid as main components and its use as a vaccine adjuvant. The present invention also relates to a method for preparing zinc risedronate micro/nano adjuvant. The present invention also relates to a chemical composition, vaccine adjuvant and vaccine composition comprising zinc risedronate micro/nano adjuvant. The present invention also relates to a use of zinc risedronate micro/nano adjuvant as a vaccine adjuvant.

8 Claims, 4 Drawing Sheets

(56) References Cited

OTHER PUBLICATIONS

Lin et al., "Calcium Phosphate Nanoparticles as a New Generation Vaccine Adjuvant," Expert Review of Vaccines 16(9):895-906 (Jul. 25, 2017).
Lin et al., "Application and Mechanism of Calcium Phosphate Nanoparticles as Vaccine Adjuvant," Jul. 15, 2019; pp. 58-63. Chinese Master's Theses Full-Text Database, Medicine & Health Sciences; English Abstract.
Luzuriaga et al., "Enhanced Stability and Controlled Delivery of MOF-Encapsulated Vaccines and Their Immunogenic Response In Vivo," ACS Applied Materials & Interfaces, 11(10): 9740-9746 (2019).
Malyala et al., "The Preparation and Physicochemical Characterization of Aluminum Hydroxide/TLR7a, a Novel Vaccine Adjuvant Comprising a Small Molecule Adsorbed to Aluminum Hydroxide," J Pharm Sci 107(6): 1577-1585 (2018).
Masson et al., "Calcium Phosphate: a Substitute for Aluminum Adjuvants," Expert Review of Vaccines 16(3):289-299 (2016).
Prasad et al., "Effects of zinc deficiency on Th1 and Th2 cytokine shifts," J Infect Dis 182 Suppl 1:S62-68 (2000).
Sanna et al., "Zinc Status and Autoimmunity: A Systematic Review and Meta-Analysis," Nutrients 10(1):68 (2018).
Sun et al., "Bisphosphonate Stabilized Calcium Phosphate Nanoparticles for Effective Delivery of Plasmid DNA to Macrophages," ACS Applied Bio Materials 3:986-996 (Jan. 6, 2020).
Wessels et al., "Zinc as a Gatekeeper of Immune Function," Nutrients 9(12):1286 (2017).
Wu et al., "Rational design of small molecules as vaccine adjuvants," Science Translational Medicine 6(263):263ra160 (2014).
Zhao et al., "Surface Phosphophilicity of Aluminum-Containing Adjuvants Probed byEfficiency for Catalyzing the P—O Bond Cleavage with Chromogenic and Fluorogenic Substrates," Analytical Biochemistry 295(1):76-81 (2001).

* cited by examiner

Aluminum adjuvant: Solution A: aluminum chloride solution; Solution B: solution of a mixture of sodium hydroxide and disodium hydrogen phosphate Risedronate zinc adjuvant: Solution A: zinc chloride solution; Solution B: solution of combined B1 and B2;

Solution B1: risedronate sodium solution; Solution B2: sodium hydroxide solution or solution of a mixture of sodium hydroxide and disodium hydrogen phosphate

Fig. 1

Zn-risedronic acid (1/1)   Zn-risedronic acid (1/0.25)   Zn-risedronic acid (1/0.125)

PREPARATION OF ZINC RISEDRONATE MICRO/NANO ADJUVANT AND USE THEREOF AS VACCINE ADJUVANT

TECHNICAL FIELD

The present invention pertains to the field of pharmaceutical technology. Specifically, the present invention relates to a zinc risedronate micro/nano adjuvant with sustained-release function formed by mineralization of zinc ions and risedronic acid as main components and its use as a vaccine adjuvant. The present invention also relates to a method for preparing zinc risedronate micro/nano adjuvant. The present invention also relates to a chemical composition, vaccine adjuvant and vaccine composition comprising zinc risedronate micro/nano adjuvant. The present invention also relates to a use of zinc risedronate micro/nano adjuvant as a vaccine adjuvant.

BACKGROUND

Adjuvants are substances that can specifically or non-specifically bind to immunogens, stimulate the body to produce long-term and effective specific immune responses, and play a complementary role. The immunobiological effects of adjuvants include reducing the amount of immunogen used, enhancing the immunogenicity of antigens, and changing the type of immune response, etc. Aluminum adjuvants are the first adjuvants approved for use in human vaccines and has a history of more than 80 years. Aluminum adjuvants are generally recognized as the most widely used, the safest and the most effective adjuvants. However, aluminum adjuvants still have shortcomings: they can only stimulate Th2 immune response and humoral immune response and have limited effect in stimulating Th1 immune response and CTL response; aluminum adjuvants have a certain of antigen specificity, and as a result, they have no adjuvant effect on vaccines against influenza virus, human immunodeficiency virus and so on; as compared with many new vaccine adjuvants, aluminum adjuvants have weaker activity, and their immune enhancement effect on most genetic engineering antigens other than virus-like particle antigens is not ideal, etc. Among the shortcomings of aluminum adjuvants, their inability to effectively stimulate the body to produce a cellular immune response restricts their application in therapeutic vaccines, and their weaker stimulation also limits their application in some of genetic engineering vaccines, such as polypeptide or nucleic acid vaccines. Based on this, people have made a series of inventions and creations on the basis of aluminum adjuvant, such as the AS04 of GlaxoSmithKline. The AS04 adjuvant system was developed by GlaxoSmithKline (GSK), in which TLR-4 (Toll like receptor 4, TLR4) agonist: 3-O-desacyl-4'-monophosphoryl lipid A (MPL), was added on the basis of aluminum adjuvants; due to the phosphorylation of its glucosamine, it has a high affinity to $Al^{3+}$ and is adsorbed by aluminum adjuvant to form a composite adjuvant. At the same time, it can stimulate a strong and balanced humoral and cellular immune response, which is of great significance for therapeutic vaccines and tumor vaccines that require cellular immune responses.

Aluminum adjuvants adsorb antigens through hydrogen bonding, hydrophobic interaction, electrostatic attraction and ligand exchange, which is one of the reasons for its immune enhancement mechanism, and is also an important factor affecting the stability of antigens. The MPL in AS04 forms a new type of composite adjuvant through the adsorption of phosphate groups with aluminum adjuvant and has been well used in clinical practice. In addition, soluble TLR7/8 small molecule agonist is likely to cause strong local and systemic toxicity when tested in humans, thus is poorly tolerated. Although insoluble small molecule agonist of TLR7/8 has good adjuvant effect, there are considerable difficulties in its production and the stabilization of its formulation. The attachment of phosphate groups can make it functionalized to obtain the ability of being adsorbed by aluminum adjuvants, and the use of chemical modification and formulation optimization can improve the pharmacokinetics of the adjuvant, which can reduce local and systemic toxicity while ensure its adjuvant activity.

The adsorption effect between the aluminum adjuvants and antigens is one of the causes for their immune enhancement mechanism. Ligand exchange is the strongest interaction force between the adjuvant and the antigen, which is generated by the ligand exchange between the phosphate group in the antigen and the hydroxy group in aluminum hydroxide or aluminum phosphate, and which is the concept of "Phosphophilicity" of aluminum adjuvant proposed by the inventor Zhao in 2001 (Analytical Biochemistry, 2001, 295(1): 76-81). Using chemical modification to attach phosphoric (phosphonic) acid groups to small-molecule immune potentiators (SMIPs), such as TLR7/8 small-molecule agonists, so that they are functionalized. and obtain the ability to be adsorbed by aluminum adjuvants, which strengthens the reservoir effect of molecular adjuvants, and reduces systemic toxicity while ensuring adjuvant activity (J Pharm Sci, 2018. 107(6): p. 1577-1585; Science translational medicine, 2014. 6(263): 263ra160). SMIPs have good application prospects in the field of vaccine adjuvants due to their clear chemical structure, easy to be modification and synthesis, and scalable production.

Similar to SMIPs, bisphosphonates (BPs) are a class of artificial compounds that have a high affinity to calcium, aluminum, zinc, and magnesium ions, and are used in the treatment of bone diseases and calcium metabolism diseases, such as osteoporosis, Paget's disease of bone, as well as hypercalcemia and bone pain caused by bone metastasis of malignant tumors. At the same time, clinical studies have shown that the use of bisphosphonates, especially risedronic acid, in the adjuvant treatment of multiple myeloma, breast cancer, kidney cancer, prostate cancer and so on can reduce the incidence of bone-related diseases in patients, the recurrence rate of cancer, and improve the survival of patients and clinical outcome. In addition, bisphosphonic acid has a positive immunoregulatory effect and exhibits adjuvant activity. The patents or inventions of bisphosphonic acid used as an immune enhancer in vaccine formulations have also been reported (Chinese patent: CN103768595B; US patent: US20170281759A1; Chinese patent: CN 108289902A).

Zinc is an important divalent metal chemical element, and its content plays an important role in the function of the immune system. Zinc at trace levels exists in about 300 enzymes involved in cell metabolism as an important structural and catalytic factor, and plays an important role in vital activities such as cell information exchange, cell division and differentiation, and immune function activation (Nutrients, 2017. 9(12): 1286; Nutrients, 2018. 10(1): 68); Wang Fudi's team published a review that described the homeostasis regulation mechanism of zinc ions in macrophages, and the imbalance of zinc homeostasis can lead to the damage of macrophages' phagocytic function and the abnormal immune response (Journal of immunology research, 2018. 2018: 6872621); in the experiment with the participation of a group of volunteers, it was found that the lack of zinc would lead to an unbalanced Th1 and Th2-biased immune response, manifested by the decreased secretion of Th1 cytokines such as IFN-γ and IL-2, while the secretion of Th2 related cytokines such as IL-4, IL-6 was not affected (J Infect Dis, 2000. 182 Suppl 1: p. S62-8); in another interesting study, researchers used a metal-organic framework (MOF) formed by zinc acetate and methylimidazole, after wrapping a viral antigen with it, not only the stability of the antigen was significantly improved, but also the immunogenicity the antigen of in mice was improved (ACS Applied Materials & Interfaces, 2019. 11(10): p. 9740-9746).

Contents of the Present Invention

The present invention provides a micro/nano adjuvant with sustained-release function that is formed by mineralization of zinc ions and risedronic acid as main components, which was referred to as zinc risedronate, its main components, its preparation method, the method for measuring its physical and chemical properties and its use in the manufacture of vaccine adjuvants, in the prophylactic vaccines and in the therapeutic vaccines.

In a specific embodiment, the zinc risedronate adjuvant of the present invention can be prepared by producing a precipitate through a reaction of zinc ions with risedronic acid, phosphate radical and hydroxide radical.

Figure 1:
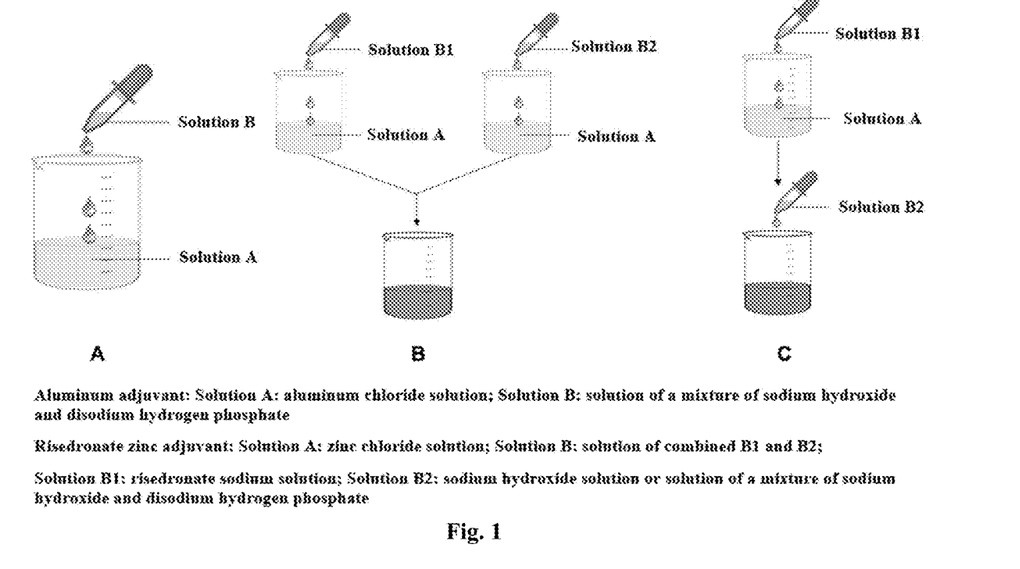
FIG. 1: schematic diagrams of three preparation processes for preparing the adjuvants.

In a specific embodiment, various mixing methods may be used to produce a precipitate through a reaction of zinc ions with risedronic acid group, phosphate radical and hydroxide radical. In a preferred embodiment, said various mixing methods include, but are not limited to, sequential precipitation, separated precipitation followed by mixing, or co-precipitation. See the schematic diagram of process: FIG. 1.

In an embodiment of the present invention, the molar concentration ratio of zinc:risedronic acid in the zinc risedronate adjuvant is generally not limited. In a preferred embodiment, the molar concentration ratio of zinc:risedronic acid in the zinc risedronate adjuvant may be (1-8):1. Preferably, the molar concentration ratio of zinc:risedronic acid is selected from 1:1, 4:1 or 8:1.

In one embodiment of the zinc risedronate adjuvant, risedronic acid has a molar concentration ratio of Zn/risedronic acid of 1:1, 4:1 or 8:1, thus forming the zinc risedronate adjuvant through a precipitation of zinc ions and phosphonic acid groups.

In another embodiment of the zinc risedronate adjuvant, the zinc risedronate adjuvant may further comprise a phosphate, for example, the risedronic acid may be replaced by phosphate in various molar proportions (not totally replaced), and a zinc risedronate adjuvant is prepared through a precipitation of zinc ions with phosphonic acid groups and phosphate radicals by various mixing methods (e.g., sequential precipitation, separated precipitation followed by mixing or simultaneous precipitation and etc.). In such zinc risedronate adjuvant, the molar concentration ratio of Zn:phosphate radical is generally not limited. In a preferred embodiment, the molar concentration ratio of Zn:phosphate radical can be (1-8):1. Preferably, the molar concentration ratio of Zn:phosphate radical is selected from 1.5:1 and 4:1, thus forming an organic-inorganic hybrid zinc risedronate adjuvant.

In another embodiment of the zinc risedronate adjuvant, the zinc risedronate adjuvant may further comprise aluminum (Al); for example, Zn may be replaced by Al in various proportions (not totally replaced), and a zinc risedronate adjuvant is prepared through a precipitation of zinc ions and aluminum ions with phosphonic acid groups, phosphate radicals or hydroxide radicals by various mixing methods (e.g., sequential precipitation, separated precipitation followed by mixing or simultaneous precipitation, etc.). In such zinc-aluminum risedronate adjuvant, the molar concentration ratio of Zn:Al is generally not limited. In a preferred embodiment, the molar concentration ratio of Zn:Al may be (0.02-1):1, and preferably, the molar concentration ratio of Zn:Al is selected from 0.375:1.

In the embodiment of the zinc risedronate adjuvant, the specific type of zinc compound is not limited, for example, it can be zinc hydroxide, zinc phosphate, zinc sulfate, zinc carbonate or other types of zinc adjuvants known in the art, as long as the zinc risedronate adjuvant is prepared by precipitation of zinc ions with phosphonic acid groups, phosphate radicals and hydroxide radicals.

In some embodiments of the zinc risedronate adjuvant, the phosphate solution can be selected from but not limited to sodium phosphate, disodium hydrogen phosphate (anhydrous, dihydrate, heptahydrate or dodecahydrate), sodium dihydrogen phosphate (anhydrous or dihydrate), potassium phosphate, dipotassium hydrogen phosphate, potassium dihydrogen phosphate, pyrophosphoric acid, polyphosphoric acid and any mixtures thereof.

In some embodiments of the zinc-aluminum risedronate adjuvant, the specific type of aluminum compound is not limited, for example, it can be aluminum hydroxide, aluminum phosphate, aluminum sulfate or other types of aluminum adjuvants known in the art, as long as the zinc-aluminum risedronate adjuvant is prepared by precipitation of zinc and aluminum ions with phosphonic acid groups, phosphate radicals and hydroxide radicals.

In one aspect, the present invention relates to a method for preparing a zinc risedronate adjuvant, which comprises:
preparing the zinc risedronate adjuvant by precipitating zinc ions through a reaction of zinc ions with phosphonic acid groups, phosphate radicals and hydroxide radicals separately or simultaneously in a soluble salt solution.

In a specific embodiment, the method comprises:
a) providing a soluble salt solution containing zinc ions,
b) co-precipitating zinc ions with phosphonic acid groups, phosphate radicals and hydroxide radicals by mixing the soluble salt solution of step a) with an alkaline solution of risedronic acid and sodium hydroxide or with an alkaline solution of risedronic acid and sodium phosphate;
in various methods, thereby obtaining a zinc risedronate adjuvant.

In some embodiments of the present invention, the soluble salt solution is generally not limited, and for example, it is preferably a solution of hydrochloric acid.

In a preferred embodiment, the method further comprises sterilizing the zinc risedronate adjuvant suspension of step b), which is formed subsequent to the mixing, by autoclaving at a high temperature high pressure condition of 121° C. for 60 minutes, cooling to room temperature and then letting stand at 2° C. to 8° C., preferably storing at 4° C. for later use. In one embodiment, the molar concentration ratio of zinc:risedronic acid in the zinc risedronate adjuvant obtained by the method of the present invention may be (1-8):1. In a preferred embodiment, the molar concentration ratio of zinc:risedronic acid is selected from 1:1, 4:1 or 8:1.

In another embodiment, in the method for preparing the zinc-aluminum risedronate adjuvant of the present invention, Al is introduced at a molar concentration ratio of Zn/Al of 0.375, and the zinc-aluminum risedronate adjuvant is prepared by a precipitation of zinc ions and aluminum ions with phosphonic acid groups, phosphate radicals and hydroxide radicals in various mixing methods (e.g., sequential precipitation, separated precipitation followed by mixing, or simultaneous precipitation and etc.).

The soluble salt solution of zinc ions as used herein may be any solution of a soluble salt of zinc ions, and is preferably a hydrochloric acid solution of zinc ions.

The risedronate solution as used herein is preferably an alkaline solution of risedronic acid and sodium hydroxide.

The method for precipitation of zinc and phosphonic acid groups as used herein may be any method in which a precipitation reaction happens by thoroughly mixing a soluble salt solution of zinc ions with an alkaline solution of risedronic acid and sodium hydroxide. Preferably, the zinc risedronate adjuvant can be prepared by any methods such as sequential precipitation, separated precipitation followed by mixing or simultaneous precipitation and etc.

The sterilization as used herein can be any method suitable for sterilizing zinc risedronate adjuvant, preferably a high temperature high pressure steam sterilization technique, for example, a sterilization performed at 121° C. for 30-60 minutes, preferably 60 minutes.

In one embodiment, the present invention also relates to methods for measuring the physical and chemical properties of the obtained zinc risedronate adjuvant. In one embodiment, the pH value, particle size, Zeta potential, point of zero charge (PZC) of particles, protein adsorption and dissociation rates, metal ion precipitation rate, organic phosphonic acid precipitation rate, in vivo and in vitro dissolution rates of the precipitates, etc., of the adjuvant are measured. The physical and chemical properties of the adjuvant can be measured by conventional techniques, for example, see U.S. Pat. No. 9,573,811; Ai Xulu et al., Analysis of physicochemical properties of three aluminum hydroxide adjuvant, "Chinese Journal of Biological Products", 2015, 28(1): 44-47; and as described in the examples herein.

In one embodiment, the zinc risedronate adjuvant as described herein has one or more of the following properties: the zinc risedronate adjuvant has a pH of 8.0-9.0 before sterilization, the zinc risedronate adjuvant has a pH of 6.0-8.0 after sterilization, the zinc risedronate adjuvant has a particle size of 1-10 μm, the zinc risedronate adjuvant has a point of zero charge of particles of 4.0-11.4, the zinc risedronate adjuvant has a metal ion precipitation rate of >99%, and the zinc risedronate adjuvant has a protein adsorption rate of >60%.

In one aspect, the present invention relates to a composition, in particular a pharmaceutical formulation or composition, comprising the zinc risedronate adjuvant as described herein.

The method of preparing the pharmaceutical formulation or composition comprises a step of combining the zinc risedronate adjuvant with a carrier and/or optionally one or more auxiliary components.

Generally speaking, the formulations are prepared by uniformly and intimately combining the zinc risedronate adjuvant with liquid carriers, or pulverized solid carriers, or both, and then, if necessary, shaping the product.

Liquid dosage forms for oral administration of the active ingredients include pharmaceutically acceptable emulsions, microemulsions, solutions, suspensions, syrups and elixirs. In addition to the zinc risedronate adjuvant, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of anhydrous sorbitan, and mixtures thereof.

Besides inert diluents, the oral compositions can also include adjuvants such as wetting agents, emulsifying and suspending agents, sweetening, flavoring, coloring, perfuming and preservative agents.

Suspension formulations, in addition to zinc risedronate adjuvant, may contain suspending agents, for example, ethoxylated isostearyl alcohols, polyoxyethylene sorbitol and esters of anhydrous sorbitan, microcrystalline cellulose, aluminum metahydroxide, bentonite, agar-agar and gum tragacanth, and mixtures thereof.

The pharmaceutical composition of the present invention for rectal or vaginal administration can be provided as a suppository, which can be prepared by mixing the zinc risedronate adjuvant with one or more suitable non-irritating excipients or carriers (including, for example, cocoa butter, polyethylene glycol, wax for suppository or salicylate), and which is solid at room temperature and liquid at body temperature, thereby melting in the rectum or vagina to release the zinc risedronate adjuvant. The formulation suitable for vaginal administration of the present invention also include vaginal suppository, tampon, cream, gel, paste, foam or spray containing suitable carriers known in the art.

The pharmaceutical composition of the present invention suitable for parenteral administration comprises the zinc risedronate adjuvant and one or more pharmaceutically acceptable sterile isotonic aqueous or non-aqueous carriers in combination with it, including solution, dispersion, suspension or emulsion or sterile powder that may be reconstituted into sterile injectable solution or dispersion prior to use, which may contain antioxidants, buffers, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size (in the case of dispersions), and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

Injectable depot forms can be made by forming microencapsule matrices of the zinc risedronate adjuvant in biodegradable polymers (such as polylactide-polyglycolide). Depending on the ratio of the zinc risedronate adjuvant to the polymer, and the nature of the particular polymer employed, the rate of release of the zinc risedronate adjuvant can be controlled. Examples of other biodegradable polymers include poly(orthoesters) and poly(anhydrides). Depot injectable formulations are also prepared by entrapping the zinc risedronate adjuvant in liposomes or microemulsions which are compatible with body tissue. The injectable materials can be sterilized for example, by filtration through a bacterial-retaining filter.

The formulations may be presented in unit-dose or multi-dose sealed containers (for example, ampoules and vials) and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In one aspect, the present invention also relates to an immunogenic composition comprising the zinc risedronate adjuvant as described herein and one or more antigens.

The immunogenic composition as used herein, when administered to a subject or an animal, stimulates a protective immune response against said one or more antigens contained therein.

In one aspect, the present invention also relates to a vaccine composition comprising the zinc risedronate adjuvant as described herein and one or more antigens.

The vaccine composition as used herein, when administered to a subject or animal, stimulates a protective immune response against, for example, a microorganism, or to efficaciously protect the subject or the animal against infection.

The vaccine composition may be used to prevent or ameliorate a pathological condition that will respond favorably to immune response modulation. Such vaccine composition may be a prophylactic vaccine or a therapeutic vaccine. Preferably, the vaccine composition includes a genetically engineered vaccine, such as a protein vaccine, such as a varicella-zoster virus recombinant protein vaccine.

In one aspect, the present invention also relates to a vaccine adjuvant comprising the zinc risedronate adjuvant as described herein. For example, such vaccine adjuvant may also include a secondary adjuvant as described below.

The term "adjuvant" or "vaccine adjuvant" as used herein refers to a substance capable of non-specifically accelerating, prolonging or enhancing an immune response against an antigen.

Advantageously, adjuvants can also reduce the number of immunization times or the amount of antigen required for protective immune response.

It is well known that an adjuvant itself will not or hardly stimulate an immune response, but an adjuvant will increase the immune response against the antigen. Therefore, the zinc risedronate adjuvant of the present invention can be combined with one or more antigens to produce an immunogenic composition or vaccine that may be used to stimulate an immune response in an individual. A variety of substances may be used as antigens in a complex or formulation, of immunogenic or vaccine type. For example, attenuated and inactivated viral and bacterial pathogens, purified macromolecules, proteins, polysaccharides, toxoids, recombinant antigens, organisms containing a foreign gene from a pathogen, synthetic peptides, polynucleotides, antibodies and tumor cells, etc. Antigens may be used in both preventive and therapeutic vaccines. Antigens include protein antigens, such as varicella-zoster virus gE glycoprotein antigen (VZV gE).

A variety of immunomodulatory molecules can also be used in combination with the zinc risedronate adjuvant of the present invention, to alter an immune response in an individual. The immunomodulators described herein refer to a class of formulations that can regulate, balance and restore the body's immune function. Commonly used immunomodulators include three major categories, which are immune promoters, immunosuppressants, and immune bidirectional modulators.

The amounts of antigen and zinc risedronate adjuvant in the vaccine composition of the present invention and the administered dose thereof are determined by techniques well known to those skilled in the pharmaceutical field, in which factors such as the following should be considered: specific antigen, age, sex, weight, specie and condition of specific animal or patient, and administration route.

In a preferred embodiment, the vaccine composition of the present invention further comprises one or more components selected from the group consisting of: surfactants, absorption promoters, water absorbing polymers, substances which inhibit enzymatic degradation, alcohols, organic solvents, oils, pH controlling agents, preservatives, osmotic pressure controlling agents, propellants, water and any mixture thereof.

The vaccine composition of the present invention may further comprise a pharmaceutically acceptable carrier. The amount of the carrier will depend upon the amounts selected for the other ingredients, the desired concentration of the antigen, the selection of the administration route (oral or parenteral), etc. The carrier can be added to the vaccine at any convenient time. In the case of a lyophilized vaccine, the carrier can, for example, be added prior to administration. Alternatively, the final product can be manufactured with the carrier.

Examples of appropriate carriers include, but are not limited to, sterile water, saline, buffers, phosphate-buffered saline, buffered sodium chloride, vegetable oils, Minimum Essential Medium (MEM), MEM with HEPES buffer, etc.

Optionally, the vaccine composition of the invention may contain conventional, secondary adjuvants in varying amounts depending on the adjuvant and the desired result.

Examples of suitable secondary adjuvants include, but are not limited to, stabilizers; emulsifiers; pH adjusters such as sodium hydroxide, hydrochloric acid, etc.; surfactants such as Tween® 80 (polysorbate 80, commercially available from Sigma Chemical Co., St. Louis, Mo.); liposomes; iscom adjuvant; synthetic glycopeptides such as muramyl dipeptides; extenders such as dextran; carboxypolymethylene; bacterial cell walls such as mycobacterial cell wall extract; their derivatives such as *Corynebacterium parvum; Propionibacterium* acne; *Mycobacterium bovis*, for example, Bovine Calmette Guerin (BCG); vaccinia or animal poxvirus proteins; subviral particle adjuvants such as orbivirus; cholera toxin; N,N-dioctadecyl-N',N'-bis(2-hydroxyethyl)-propanediamine (pyridine); monophosphoryl lipid A; dimethyldioctadecylammonium bromide (DDA, commercially available from Kodak, Rochester, N.Y.); synthetics and mixtures thereof.

Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines compositions.

For the purpose of this invention, these adjuvants are identified herein as "secondary" merely to contrast with the above-described zinc risedronate adjuvant, because the combination of the zinc risedronate adjuvant and the antigenic substance can significantly increase the humoral immune response to the antigenic substance. The secondary adjuvants are primarily included in the vaccine formulation as processing aids, although certain adjuvants do possess immunologically enhancing properties to some extent and have a dual purpose.

Conventional preservatives can be added to the vaccine composition in effective amounts ranging from about 0.0001% to about 0.1% by weight. Depending on the preservative employed in the formulation, amounts below or above this range may be useful. Typical preservatives include, for example, potassium sorbate, sodium metabisulfite, phenol, methyl paraben, propyl paraben, thimerosal, etc.

The choice of inactivated, modified or other type of vaccine composition and preparation of the improved vaccine composition formulation of the present invention are known or readily determined by those of ordinary skill in the art.

As a general rule, the vaccine composition of the present invention can be conveniently administered orally, parenterally (subcutaneously, intramuscularly, intravenously, intradermaly or intraperitoneally), intrabuccally, intranasally, or transdermally. The route of administration contemplated by the present invention will depend upon the antigenic substance and the co-formulants. For instance, if the vaccine composition contains saponins, while non-toxic for oral or intranasal administration, care must be taken not to inject the sapogenin glycosides into the blood stream as they function as strong hemolytics. Also, many antigens will not be effective if taken orally. Preferably, the vaccine composition is administered intramuscularly.

The dosage of the vaccine composition will be dependent notably upon the selected antigen, the route of administration, species and other standard factors. It is contemplated that a person of ordinary skill in the art can easily and readily titrate the appropriate dosage for an immunogenic response for each antigen, to determine the effective immunizing amount and administration route.

As a vaccine adjuvant, the zinc risedronate adjuvant of the present invention can improve the effectiveness of the vaccine by enhance the immunogenicity of weaker antigens (e.g., highly purified or recombinant antigens), by reduce the amount of antigens required for immune response, or by reduce the immunization frequency required for protective immunization. The zinc risedronate adjuvant of the present invention can improve the effectiveness of the vaccine in individuals (e.g., neonates, elderly, and immunocompromised individuals) with reduced or weakened immune responses and can enhance the effectiveness of the vaccine in target tissues. Alternatively, the zinc risedronate adjuvant of the present invention can promote cell-mediated immune response and/or humoral immune response by triggering a specific cytokine profile.

The combination of an antigen and/or immunomodulatory molecule and the zinc risedronate adjuvant of the present invention can be tested in a variety of preclinical toxicological and safety studies well known in the art.

For example, such a combination can be evaluated in an animal model in which the antigen has been found to be immunogenic and that can be reproducibly immunized by the same route proposed for human clinical testing.

The combination of antigen and/or immunomodulatory molecule and the risedronic acid adjuvant of the present invention can be tested, for example, by an approach set forth by the Center for Biologies Evaluation and Research/Food and Drug Administration and National Institute of Allergy and Infectious Diseases (Goldenthal, K L et al. AID Res Hum Retroviruses, 9: S45-9 (1993)).

Those skilled in the art will know how to determine, for a particular combination of antigen and/or immunomodulatory molecule with the composite adjuvant of the invention, the appropriate antigen payload, route of immunization, dose, purity of antigen, and vaccination regimen useful to treat a particular pathological condition in a particular animal species.

The immunogenic composition or a vaccine of the invention, for inducing an immune response, can be administered as a solution or suspension together with a pharmaceutically acceptable medium.

Such a pharmaceutically acceptable medium may be, for example, water, phosphate buffered saline, normal saline or other physiologically buffered saline, or other solvent or vehicle such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside (such as Quil A).

The immunogenic composition or vaccine of the invention can be administered by a variety of routes to stimulate an immune response. For example, the immunogenic composition or vaccine can be delivered subcutaneously, intradermaly, intralymphatically, intramuscularly, intratumorally, intravesically, intraperitoneally and intracerebrally.

Those skilled in the art will know how to select appropriate delivery routes for particular formulations of the zinc risedronate adjuvant of the invention.

In a preferred embodiment of the present invention, the vaccination method for the treatment or prevention of infection in a mammal comprises use of the vaccine of the present invention, in which the vaccine will specifically be administered intramuscularly. The vaccine may be administered as a single dose, or preferably administered several times, for example, two, three or four times, per week or per month according to the primary immunization/booster immunization strategy. The appropriate dose depends on a variety of parameters.

In one aspect, the present invention also relates to a use of the zinc risedronate adjuvant as described herein for the manufacture of a vaccine adjuvant, a pharmaceutical composition, an immunogenic composition or a vaccine composition. Preferably, the vaccine comprises protein vaccine, such as varicella-zoster virus protein recombinant vaccine.

SPECIFIC MODES FOR CARRYING OUT THE PRESENT INVENTION

The following describes the embodiments of the present invention in detail in conjunction with the examples. For those not indicating specific conditions in the examples, they shall be carried out in accordance with the conventional conditions or the conditions suggested by the manufacturer. The reagents or instruments used without the manufacturer's indication are all conventional products that can be purchased commercially.

Preparation Example 1: Preparation of Zinc Risedronate Adjuvant (Zn-Risedronic Acid (1/0.25))

Risedronate sodium ($C_7H_{10}NNaO_7P_2$): purchased from Hunan Huateng Pharmaceutical Co., Ltd.
Anhydrous zinc chloride ($ZnCl_2$): purchased from Xilong Chemical
Disodium hydrogen phosphate dodecahydrate ($Na_2HPO_4 \cdot 12H_2O$): purchased from Xilong Chemical
Sodium hydroxide (NaOH): purchased from Xilong Chemical
Preparation of Solutions:
According to a molar concentration ratio of Zn/risedronic acid of 1:0.25, 50 mL of a 31.11 mM zinc chloride solution was prepared and defined as Solution A; 50 mL of a solution (7.78 mM risedronic acid+36 mM sodium hydroxide+15.55 mM disodium hydrogen phosphate) was prepared and defined as Solution B. Solution A and Solution B were filtered with 0.22 μm filter membrane for later use.
Preparation of Zn-Risedronic Acid (1/0.25) Adjuvant Suspension and Determination of its Physical and Chemical Properties:
Solution A and Solution B were used to form a zinc risedronate adjuvant suspension according to the scheme as shown in FIG. 1A, that was, the prepared Solution B was added dropwise to Solution A at a volume ratio of 1:1 until all was added, forming a suspension.
After the mixing step according to FIG. 1A, the obtained zinc risedronate adjuvant was sterilized once by high-pressure steam at 121° C. for 60 min, and its physical and chemical properties such as pH value, particle size and particle morphology after sterilization were measured.

Preparation Example 2: Preparation of Zinc Risedronate Adjuvant (Zn-Risedronic Acid (1/1))

The source of reagents can be found in Preparation Example 1.
Preparation of Solutions:
According to a molar concentration ratio of Zn/risedronic acid of 1:1, 50 mL of a 31.11 mM zinc chloride solution was prepared and defined as Solution A; 50 mL of a solution (31.11 mM risedronic acid+60 mM sodium hydroxide) was prepared and defined as Solution B. Solution A and Solution B were filtered with 0.22 μm filter membrane for later use.
Preparation of Zn-Risedronic Acid (1/1) Adjuvant Suspension and Determination of its Physical and Chemical Properties:
Please refer to Preparation Example 1 for details.

Preparation Example 3: Preparation of Zinc Risedronate Adjuvant (Zn-Risedronic Acid (1/0.125))

The source of reagents can be found in Preparation Example 1.
Preparation of Solutions:
According to the molar concentration ratio of Zn/risedronic acid of 1:0.125, 1 L of 124.44 mM zinc chloride solution was prepared and defined as Solution A; 1 L of solution (15.56 mM risedronic acid+60 mM sodium hydroxide+184 mM disodium hydrogen phosphate) was prepared and defined as Solution B. Solution A and Solution B were filtered with 0.22 μm filter membrane for later use.
Preparation of Zn-Risedronic Acid (1/0.125) Adjuvant Suspension and Determination of its Physical and Chemical Properties:
Please refer to Preparation Example 1 for details.

Preparation Example 4: Preparation of Aluminum Adjuvant Al-002

Preparation of solutions: the source of reagents can be found in Preparation Example 1.
According to the molar concentration ratio of phosphate radical/Al of 0.3:1, 50 mL of a 62.22 mM aluminum chloride solution was prepared and defined as Solution A; 50 mL of 9.33 mM disodium hydrogen phosphate solution (50 mM sodium hydroxide) was prepared and defined as Solution B. Solutions were filtered with 0.22 μm filter membrane for later use.
Preparation of Aluminum Adjuvant Al-002 Suspension
Solution A and Solution B were prepared in a volume ratio of 1:1. The preparation was carried out according to the scheme of FIG. 1A in which the prepared Solution B was added dropwise to Solution A at a volume ratio of 1:1 until all was added, forming a suspension. The suspension obtained after mixing was sterilized at 121° C. for 60 min.

Preparation Example 5: Preparation of Aluminum Adjuvant Al-001-840

Preparation of solutions: the source of reagents can be found in Preparation Example 1.
According to a phosphate/Al molar concentration ratio of 0.15, 0.5 L of a 124 mM aluminum chloride solution was prepared and defined as Solution A; 0.5 L of an 18.6 mM disodium hydrogen phosphate solution was prepared and defined as Solution B, which also contained 150 mM sodium hydroxide. Solutions were filtered with 0.22 μm membrane for later use.
Aluminum adjuvant Al-001-840 suspension was prepared by the same method referring to the preparation of aluminum adjuvant Al-002 suspension.

Example 1: Determination of Physical and Chemical Properties of Zinc Risedronate Adjuvant (Zn-Risedronic Acid (1/0.125))

The zinc risedronate suspension obtained after mixing was sterilized once at 121° C. for 60 minutes, and the physical and chemical properties such as pH value, particle size and particle morphology, metal ion precipitation rate and other physical and chemical properties after sterilization were measured.

The following detection methods were applicable to any Zn/risedronic acid molar ratio, that was, any zinc risedronate adjuvant, such as zinc risedronate adjuvant doped with inorganic phosphoric acid;

(1) Observation of Adjuvant Particle Morphology

After the risedronate zinc adjuvant was diluted 50 times with deionized water, the observation was performed with a JEM-2100 transmission electron microscope (TEM) of Japan Electronics. The specific steps were as follows: dropping the adjuvant sample on a copper mesh coated with carbon film, allowing 10 minutes for absorption, wiping off the residual liquid with filter paper, sending samples to the sample chamber of the transmission electron microscope to observe the morphology of the sample, and taking photos for further analysis.

Figure 2:
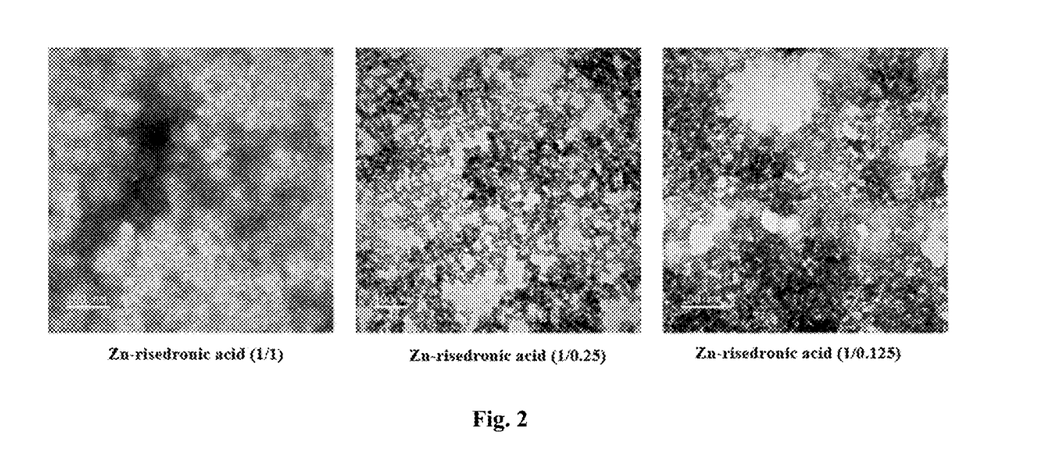
FIG. 2: electron microscopic view of the zinc risedronate adjuvant.

Experimental results: As shown in FIG. 2, Zn-risedronic acid (1/1) adjuvant had an amorphous cluster shape, while in the Zn-risedronic acid (1/0.25) and Zn-risedronic acid (1/0.125) adjuvants, spherical nano-core particles could be clearly seen.

(2) pH Measurement

The samples to be tested was taken, equilibrated at room temperature for at least 30 minutes, and measured with a Sartorius pH glass electrode.

Standard buffer (pH7.00), standard buffer (pH4.01) and standard buffer (pH10.01) were selected to calibrate the instrument according to the requirements of the instruction manual.

The "Mode" button could be pressed to switch between pH and mV modes. Usually, the pH mode was selected when determining the pH value of a solution.

The "SETUP" button was pressed until the display showed Clear buffer, and then the "ENTER" button was pressed to confirm and clear the previous calibration data.

The "SETUP" button was pressed until the display showed the buffer solution group "4.01, 7.00, 10.01", and then the "ENTER" button was pressed to confirm.

The electrode was taken out of the electrode storage solution carefully, the electrode was rinsed thoroughly with deionized water, and the water on the surface was dried with filter paper after well rinsed (be careful not to wipe the electrode).

The electrode was immersed in the first buffer solution (pH 7.00), until the value was stable and "S" appeared, then the "STANDARDIZE" button was pressed, until the instrument was automatically calibrated. After the calibration was successful, "7.00" and the electrode slope were displayed.

The electrode was taken out from the first buffer solution, and the electrode was rinsed thoroughly with deionized water, and the electrode was immersed in the second buffer solution (pH 4.01) in sequence, until the value was stable and "S" appeared, then the "STANDARDIZE" button was pressed, until the instrument was calibrated automatically. After the calibration was successful, "4.01 7.00" and the message "Slope" displayed. Slope displayed the measured electrode slope value, which was acceptable in the range of 90-105%.

If there was a big deviation from the theoretical value, an error message (Err) would be displayed, then the electrode should be cleaned, and the above steps should be repeated for calibration.

The above operations were repeated to complete the third point (pH 10.01) calibration.

After the calibration was completed, the electrode was rinsed thoroughly with deionized water, and then dried gently with filter paper. The sample solution was shaken evenly, the glass electrode was immersed in the sample solution, until the pH value change no more than ±0.05 within 1 minute, and then the reading was confirmed.

The sample solution was shaken evenly and the measurement was carried out again. The difference between the two pH values should not exceed 0.1. The average of the two readings was taken as the pH value of the test product.

Experimental Results: Zn-Risedronic Acid (1/0.125) Adjuvant had a pH of 6.9-7.3 Before Sterilization and 6.4-6.8 after Sterilization;

(3) Determination of Particle Size

Beckman LS 13320 laser particle size analyzer was turned on and warmed up for 15 minutes.

The analyzer control software were started and the closed compartment of the sample cell were opened, the sample cell was taken from the sample tank and added with 12 mL of purified water.

The sample cell was placed on the sample tank and the compartment door was closed.

"start cycle" was clicked, "Measure Offsets", "Align", "Measure Background" were selected in turn, and finally "start" was clicked, "OK" in the pop-up dialog box was clicked to start the calibration of blank background.

The sample cell was taken out, and added with a certain amount of standard sample (come with the analyzer); "start cycle" was clicked, "Measure Loading", "Enter Sample Info", "Enter run setting", "start runs" were selected in turn, and finally "start" was clicked, the name of the standard sample was input in the pop-up dialog box, "OK" was clicked when "Obscuration" parameter in the software was 8% to 12%, so the measurement of the standard sample was carried out.

In order to ensure the accuracy and reliability of the experimental data, the blank background should be calibrated and the size of the standard sample should be measured before each measurement was performed.

The closed compartment of the sample cell was opened and the sample cell was taken out.

The aqueous solution containing the standard sample in the sample cell was discarded, and deionized water was added into the sample cell to clean the sample cell 3 times.

After cleaning, 12 mL of deionized water was added, and the sample cell was placed on the sample tank, and the compartment door was closed.

"start cycle" was clicked, "Measure Offsets", "Align", "Measure Background" were selected in turn, and finally "start" was clicked, "OK" in the pop-up dialog box was clicked to start the calibration of blank background.

The sample cell was taken out, added with a certain volume of a test sample, the sample test compartment door was opened, the sample cell was placed on the sample tank and the compartment door was closed.

"start cycle" was clicked, "Enter Sample Info", "Enter run setting", "start runs" were selected in turn, and finally "start" was clicked, the name of the standard sample was input in the pop-up dialog box, "OK" was clicked when "Obscuration" parameter in the software was 8% to 12%, the particle sizes of samples that were measured were recorded.

Figure 3:
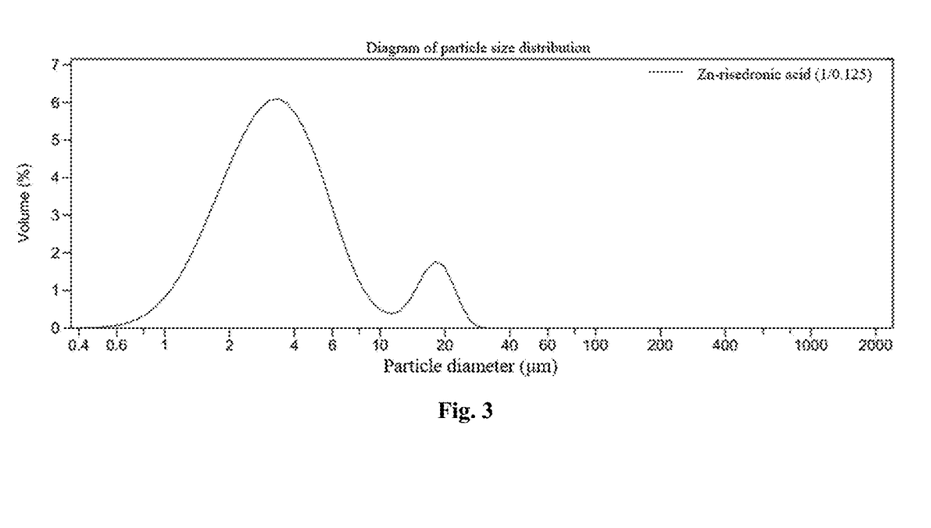
FIG. 3: particle size of the zinc risedronate adjuvant.

Experimental results: As shown in FIG. 3, taking the Zn-risedronic acid (1/0.125) adjuvant as an example, the particle size was between 0.4-30 μm, and most of the particles had size of 6-7 μm.

(4) PZC Detection:

Instrument for Measurement: Nanobrook Omni (Brookhaven)

Experimental operation: 0.1M NaOH/1% $HNO_3$ were used to adjust the pH of Zn-risedronic acid (1/0.125) to: 6.00/5.50/5.00/4.50/4.00/3.50/3.00/2.50/2.00.

Passivated electrode: 3-4 mL of the adjuvant was added to the sample tube. After the electrode was inserted, the cycle in the SOP was set to 50, and the instrument was run to passivate the electrode.

Sample measurement: After the electrode was taken out, its lower end was rinsed with deionized water, and then the corresponding sample was added, the cycle was set to 15 in the SOP, the measure was set to 3, the pH was set to the corresponding pH of each sample, and the instrument was run.

Data processing: the corresponding Zeta potentials under different pH values were got, the software that came with the instrument was run to get the PZC values.

Results: The PZC of Zn-risedronic acid (1/0.125) adjuvant was 4.11.

(5) Determination of Adsorption Rate of Zinc Risedronate Adjuvant

Plotting standard curve for BSA standard: 150 mM NaCl was used as dilution buffer, the BSA standard (2 mg/mL) was serially diluted, and the absorbance at 280 nm was detected with UV2100 pro. The OD280 showed a high accuracy at 0.2-0.8 (broaden to 0.2-1.5).

BSA gradient dilution (EP): 150 mM NaCl was used as dilution buffer, a certain amount of BSA sample was weighed and diluted to the concentration gradient specified in EP: 0.5 mg/mL, 1 mg/mL, 2 mg/mL, 3 mg/mL, 5 mg/mL, 10 mg/mL, for later use.

BSA was mixed with adjuvant at a ration of BSA: adjuvant=3:1 (volume ratio), which was set as the usage condition for the measurement of adsorption rate; after the adjuvant was shaken evenly, it was mixed with different concentrations of BSA according to the experimental conditions, and the adsorption at room temperature was performed for 1 hour, and shaking was performed 5 times during the period; a centrifugation was performed at 13000 rpm/min for 3 minutes, the supernatant was taken afterwards, for later use.

Determination of protein concentration: Lowry method was used to determine the protein concentration in EP. In this experiment, according to the practical situation, UV2100pro was used to directly determine the absorbance of the supernatant at 280 nm, the reading was kept between 0.2-0.8, otherwise the supernatant should be diluted.

Calculation of adsorption rate: adsorption rate=[1−$OD_{280(supernatant\ dilution\ factor\ X)}/OD_{280(when\ the\ adsorption\ rate\ of\ dilution\ X\ is\ 0)}$]*100

Experimental results: Taking Zn-risedronic acid (1/0.125) as an example, firstly, the BSA standard curve was measured. The content of BSA in the adjuvant supernatant was calculated according to the standard curve, and the adsorption rate of Zn-risedronic acid (1/0.125) adjuvant to BSA was calculated according to the absorption formula, which could reach about 70% when BSA was 0.5 mg/mL.

TABLE 1

Adsorption rate of Zn-risedronic acid (1/0.125) adjuvant

| | BSA concentration (mg/mL) | | | | | |
|---|---|---|---|---|---|---|
| | 0.50 | 1.00 | 2.00 | 3.00 | 5.00 | 10.00 |
| BSA absorption rate | 66% | 53% | 39% | 34% | 19% | 3% |

Example 2: Determination of Metal Ion Precipitation Rate of Zinc Risedronate Adjuvant Method: Flame atomic absorption spectrometry, by measuring the content of zinc element in the supernatant of adjuvant, its meal ion precipitation rate was calculated.

The flame method (D2 lamp background correction) was used to determine the zinc content in the risedronate zinc adjuvants and the determination procedure was standardized. The detection instrument was an atomic absorption spectrophotometer: Shimadzu AA6300C (P/N 206-52430).

Preparation of standard solution and sample to be determined: preparation of standard curve: the original concentration of zinc standard was 500 μg/mL, and it was diluted with 0.1 M hydrochloric acid solution to obtain 500 ng/mL, 1000 ng/mL, 1500 ng/mL, 2000 ng/mL and 2500 ng/mL standards.

The preparation of the solution to be tested: the sample was diluted 400 times with 0.1M hydrochloric acid solution and mixed well by a vortex mixer under vibration.

The Zn-risedronic acid (1/0.125) adjuvant was centrifuged at 13000 r/min for 10 min and the supernatant was removed. The sample was diluted 5 times with ultrapure water for measurement. The measurement process was as follows:

Operation Method of AA-6300C and Usage of WizAArd Software:

Power turning on: the computer, AA-6300C power switch, air compressor switch (the pressure was set at 0.35 MPa), and ventilation system switch were turned on;

Acetylene opening: the acetylene valve was slowly opened to ensure that the primary pressure was 0.5 MPa and the secondary pressure was 0.1 MPa;

Basic operation procedure of WizAArd software: log in WizAArd→select element→at "unconnected instrument/ send parameter" page, click <connect/send parameter>→set in "instrument initialization" page→check and tick each of items in "flame analysis instrument check catalog", click <OK>→set wavelength [213.86], slit width [0.7], lighting method [emission], [lamp position setting] in "optical parameters" page to ensure the actual position and preset position of the Zn hollow cathode lamp be identical, select [lamp on]→line search→burner origin position adjustment-→select [parameter] in the menu bar→[edit parameter] →change the lighting method to <BGC-D2>→line search→ignition: after ensuring that C2H2 was turned on and the pressure met the requirements, press the PURGE and IGNITE buttons on the host at the same time until ignition→auto zero→set the blank group (BLK), standard product (STD), and test sample (UNK) on the MRT worksheet, input the theoretical concentration of the standard and the name of the sample, and manually load the sample through the sample tube extended from the nebulizer, set the sample volume at least 1 mL each time, select [start] to test→stop the flame→save the data and disconnect the instrument from the computer→shut down;

Experimental results: Taking Zn-risedronic acid (1/0.125) as an example.

TABLE 2

Drawing of standard curve of zinc concentration and Abs

| | Zinc standard concentration (X, ng/mL) | | | | | |
|---|---|---|---|---|---|---|
| | 0 | 500 | 1000 | 1500 | 2000 | 2500 |
| Abs (y) | 0.017 | 0.093 | 0.161 | 0.248 | 0.314 | 0.379 |
| Standard curve formula | y = 0.0001x + 0.0191, $R^2$ = 0.9984 | | | | | |

TABLE 3

Test results of zinc precipitation rate
in Zn-risedronic acid (1/0.125) adjuvant

| Sample | Abs | Zinc content of supernatant (μg/mL) | Total zinc content of adjuvant (μg/mL) | Zinc precipitation rate (%) |
|---|---|---|---|---|
| Zn-risedronic acid (1/0.125) | 0.155 | 6.8 | 4067 | 99.83% |

Example 3: Determination of Risedronic Acid Precipitation Rate of Zinc Risedronate Adjuvant Method: UV Spectrophotometry, Instrument: UV800 (Beckman Coulter).

Risedronic acid contained a pyridine ring, which had a maximum absorption peak at 260 nm. The specific process of detecting the supernatant of the adjuvant at 260 nm by an ultraviolet spectrophotometer was as follows:

First, 2.374 mg/mL sodium risedronate solution (the content of sodium risedronate added in Zn-risedronate adjuvant (1/0.125)) was prepared with physiological saline solution, diluted with physiological saline to 0.08 mg/mL, 0.06 mg/mL, 0.04 mg/mL, 0.03 mg/mL, 0.02 mg/mL, 0.015 mg/mL, 0.01 mg/mL, and measured at the wavelength of 260 nm to obtain $OD_{260}$ values, respectively. At the same time, we centrifuged the Zn-risedronic acid (1/0.125) at 13000 rpm for 10 min and then took the supernatant. The supernatant of the adjuvant was in an isotonic environment, and detected at a wavelength of 260 nm to obtain the absorbance of sodium risedronate in the supernatant. The results were as follows:

TABLE 4

Risedronate sodium concentration and $OD_{260}$ standard curve

| | Risedronate sodium standard concentration (x, mg/mL) | | | | | | |
|---|---|---|---|---|---|---|---|
| | 0.01 | 0.015 | 0.02 | 0.03 | 0.04 | 0.06 | 0.08 |
| $OD_{260}$ (y) | 0.1316 | 0.1946 | 0.2704 | 0.3872 | 0.5365 | 0.7879 | 1.0185 |
| Standard curve plotting | y = 12.777x + 0.0098, $R^2$ = 0.9989 | | | | | | |

TABLE 5

Risedronic acid precipitation rate of
Zn-risedronic acid (1/0.125) adjuvant

| Sample | $OD_{260}$ | Risedronic acid content of supernatant (μg/mL) | Total risedronic acid content of adjuvant (μg/mL) | Risedronic acid precipitation rate (%) |
|---|---|---|---|---|
| Zn-risedronic acid (1/0.125) | 0.0141 | 0.3 | 2373 | 99.3 |

Example 4: Determination of Adjuvant Activity of Zinc Risedronate Adjuvant Combined with Recombinant Protein VZV gE The prepared Zn-risedronic acid adjuvants were used as adjuvants, in which the molar concentration ratio of Zn/risedronic acid were 1:1 and 1:0.25 respectively, and they were separately used as adjuvants and mixed with VZV gE antigen at volume ratio of 1:1 to form vaccines, and then the vaccines were administered by intramuscular injection to mice to determine the specific antibody titers produced. The specific method was as follows:

Experimental animals: Balb/C mice, 6-8 weeks, 5 mice/group, female.

Experimental groups: (1) aluminum adjuvant group (Al-002); (2) Zn-risedronic acid (1/0.25) group; (3) Zn-risedronic acid (1/1) group;

Immunization protocol: antigen 5 μg/mouse, adjuvant and VZV gE antigen were mixed at a volume ratio of 1:1 to form a vaccine, and then intramuscularly injected mice, 100 μL per mouse, and 50 μL on each hind leg. The immunization was performed in the $0^{th}$, $2^{nd}$ and $4^{th}$ week, that was, 2 weeks after the first immunization of the animals according to the immunization grouping, blood samples were collected from eye socket to determine the specific antibody titers in serum.

Antibody titers were measured in the $2^{nd}$ week after the first immunization, booster immunization was performed in the $2^{nd}$ week, blood samples were taken from eye socket 2 weeks after the second immunization, the specific antibody titers in serum were measured, the third immunization was performed at the same time, blood samples were taken from eye socket 2 weeks later, and antibody titers in serum were measured by ELISA.

Determination of Antibody Binding Titer by Enzyme-Linked Immunosorbent Assay (ELISA):

1. Antigen coating solution: 1× PB 7.4 buffer solution (4.343 g of $Na_2HPO_4.7H_2O$; 0.456 g of $NaH_2PO_4$).
2. Washing solution: PBST, INNOVAX Co. ELISA kit
3. Blocking solution: 2× ED (Enzyme Dilution): 1×PBS+0.5% casein+2% gelatin+0.1% preservative (proclin-300), diluted to 1× with ultrapure water or distilled water for sealing and sample dilution.
4. Color development solution A: INNOVAX Co. ELISA kit.
5. Color development solution B: INNOVAX Co. ELISA kit.
6. Stop solution: INNOVAX Co. ELISA kit.

Experiment Procedure:

(1) Coating plate: VZV gE antigen was diluted with PB7.4 coating buffer solution to a certain concentration. It was added to a 96-well polystyrene plate by 100 μL/well, and the plate was coated overnight at 4° C.

(2) Blocking: the coating solution in the well was discarded, the plate was washed with PBST washing solution once, spin-dried, added with the blocking solution by 200 μL/well, and blocking was performed for 4 hours at room temperature.

(3) Adding serum of a certain degree of dilution: the blocking solution in the well was discarded, the plate was washed with PBST once, spin-dried, the first well was added with the serum to be tested by 150 μL/well, each of the following well was added with ED diluent by 100 μL/well, diluted at a gradient of 3 times, incubated and reacted at 25° C. for 1 h.

(4) Adding enzyme-labeled antibody (GAM-HRP): the serum diluent in the well was discarded, the plate was washed 5 times with PBST, spin-dried, added with enzyme-labeled antibody (GAM-HRP, V:V=1:5000) by 100 μL/well, incubated and reacted at 25° C. for 1 h.

(5) Color development: the secondary antibody in the well was discarded, the plate was washed 5 times with PBST, spin-dried, added with 100 μL/well of a color development solution, an equal volume mixed A and B, and reacted at 25° C. for 10 min.

(6) Stopping: 2 M sulfuric acid stop solution was added by 50 μL/well to stop the reaction.

(7) Reading plate: dual wavelengths of 450 nm and 630 nm were set as the measuring wavelengths on microplate reader and the OD value of each reaction well was measured.

Figure 4:
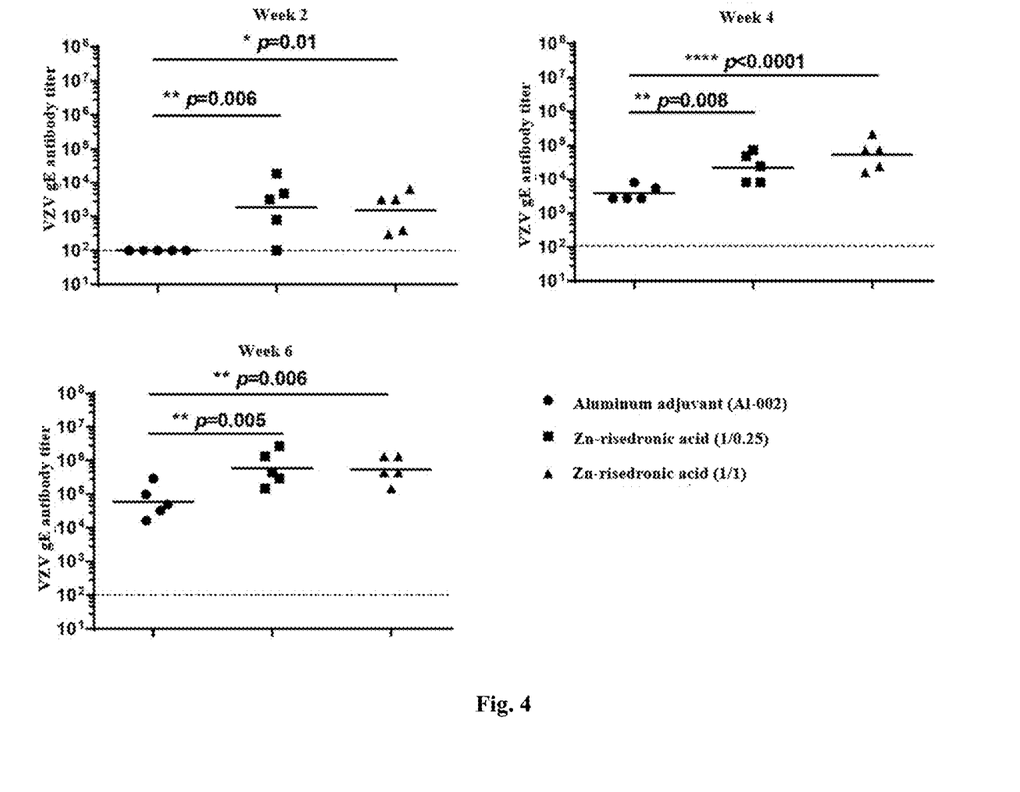
FIG. 4: determination of the adjuvant activity of zinc risedronate adjuvant combined with recombinant VZV gE protein, mean±SD: n=5, *p<0.05; p<0.01; *p<0.001, ****p<0.0001.

The experimental results were shown in FIG. 4:

Two weeks after the one dose of immunization of mice, the antibody titers of the Zn-risedronic acid adjuvant groups (1/0.25, 1/1) were higher than that of the control group, that was, they were more than 10 times that of the aluminum adjuvant group, showing features of fast onset of action. After two doses of immunization, advantages of humoral immune response enhancement were still noticeable. At the $4^{th}$ week, the antibody titer of the Zn-risedronic acid adjuvant group (1/0.25) was 7.5 times that of the aluminum adjuvant group, and the Zn-risedronic acid adjuvant group (1/1) was 18 times that of the aluminum adjuvant group. After three doses of immunization, at the 6th week, the antibody titer of the Zn-risedronic acid adjuvant group (1/0.25) was 10 times that of the control group, and the Zn-risedronic acid adjuvant group (1/1) was 7.5 times that of the control group.

Example 5: Effect of Immunization of Mice with Zinc Risedronate Adjuvant Combined with Recombinant Protein VZV gE on Specific Antibody Isotypes The prepared Zn-risedronic acid adjuvant was used as an adjuvant, in which the Zn/risedronic acid molar concentration ratio was 1:0.25, it was used as an adjuvant in combination with VZV gE antigen to inject intramuscularly into mice, and the specific antibody titer produced was measured. The specific method was as follows:

Experimental animals: Balb/C mice, 6-8 weeks, 5 mice/group, female.

Experimental groups: (1) aluminum adjuvant group (Al-002); (2) Zn-risedronic acid (1/0.25) group;

Immunization protocol: antigen 5 μg/mouse, adjuvant and VZV gE antigen were mixed at a volume ratio of 1:1 to form a vaccine, and then intramuscularly injected mice, 100 μL per mouse, and 50 μL on each hind leg. Immunization was performed at the $0^{th}$ $2^{nd}$ and $4^{th}$ week, after 3 injections of immunization was completed, blood samples were collected from eye socket after 2 weeks for testing, and ELISA was used to determine the levels of specific antibody isotypes in serum.

Experimental Materials:
1. Antigen coating solution: 1× PB 7.4 buffer solution (4.343 g of $Na_2HPO_4.7H_2O$; 0.456 g of $NaH_2PO_4$).
2. Washing solution: PBST, ELISA kit from Beijing Wantai Company.
3. Blocking solution: 2× ED (Enzyme Dilution): 1×PBS+ 0.5% casein+2% gelatin+0.1% preservative (proclin-300), diluted to 1× with ultrapure water or distilled water for sealing and sample dilution.
4. Color development solution A: ELISA kit from Beijing Wantai Company.
5. Color development solution B: ELISA kit from Beijing Wantai Company.
6. Stop solution: Beijing Wantai Company ELISA kit.

Experiment Procedure:
(1) Coating plate: the VZV gE antigen was diluted with PB7.4 coating buffer solution to a certain concentration, added to a 96-well polystyrene plate by 100 μL/well, and the plate was coated overnight at 4° C.

(2) Blocking: the coating solution in the well was discarded, the plate was washed once with PBST, spin-dried, added with blocking solution by 200 μL/well, and blocking was performed for 4 hours at room temperature.

(3) Adding serum to be tested: the blocking solution in the well was discarded, the plate was washed once with PBST, spin-dried, added with the serum to be tested at a certain degree of dilution by 100 μL/well, incubated and reacted for 1 h at 25° C.

(4) Adding enzyme-labeled antibody: the serum diluent in the well was discarded, the plate was washed 5 times with PBST, spin-dried, added with enzyme-labeled antibody that specifically recognized each antibody isotype (IgG1, V:V=1:30000; IgG2a, V:V=1:1000; IgG2b, V:V=1:1000) by 100 μL/well, incubated and reacted at 25° C. for 1 h.

(5) Color development: the enzyme-labeled antibody in the well was discarded, the plate was washed 5 times with PBST, spin-dried, added with a color development solution, that was an equal volume mixed A and B diluted by 3 times, by 100 μL/well, reacted at 25° C. for 10 min.

(6) Stopping: 50 μL/well of 2 M sulfuric acid stop solution was added to stop the reaction.

(7) Reading plate: dual wavelengths of 450 nm and 630 nm were set as the measuring wavelengths on microplate reader, and the OD value of each reaction well was measured.

Figure 5:
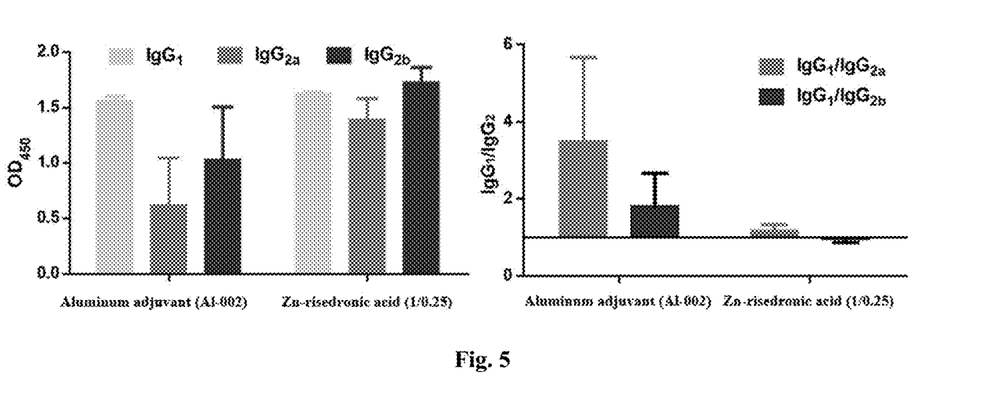
FIG. 5: effect of zinc risedronate adjuvant combined with recombinant VZV gE protein on mouse antibody isotypes, mean±SD: n=5, *p<0.05; p<0.01; *p<0.001, ****p<0.0001.

The experimental results were shown in FIG. 5:

Using the experimental procedure described in Example 4, mice were immunized by intramuscular injection with zinc risedronate adjuvant or aluminum adjuvant in combination with recombinant protein VZV gE, and the immunization procedure was the same as that of Example 4. After the three injections, blood samples were collected after 2 weeks, and the results of level of each isotypes of mouse serum antibody were shown in FIG. 5. Compared with the aluminum adjuvant group, the zinc risedronate adjuvant group could stimulate more intense IgG2a and IgG2b isotypes antibody levels, and the ratios of IgG1 to IgG2a and IgG2b were lower than that of the aluminum adjuvant group, indicating that it had a certain stimulating effect on Th1 immune pathway.

Example 6: Determination of Adjuvant Activity of Zinc Risedronate Adjuvant Combined with Hepatitis B Therapeutic Protein Using the experimental procedure described in Example 4, mice were immunized with zinc risedronate adjuvant in combination with hepatitis B therapeutic protein by intramuscular injection, and serum antibody titers were detected. The specific method was as follows:

Experimental animals: Balb/C mice, 6-8 weeks, 5 mice/group, female.

Experimental groups: (1) normal saline; (2) aluminum adjuvant group (Al-001-840); (3) sodium risedronate group; (4) Zn-risedronic acid (1/0.125) group; among them the content of sodium risedronate in the group (3) was the same as the zinc risedronate in the group (4). Please refer to Preparation Example 3 for details.

Immunization protocol: antigen 1.2 μg/mouse, adjuvant and hepatitis B therapeutic protein were mixed at a volume ratio of 1:1 to form a vaccine, and then injected intramuscularly to mice, 150 μL per mouse, and 75 μL on each hind leg. The immunization was performed on the $0^{th}$, $2^{nd}$, $3^{rd}$, $4^{th}$, $5^{th}$ and $6^{th}$ week, 1.2 μg of antigen per mouse, blood samples were collected from eye socket after the 6th week, and ELISA was used to determine the levels of specific antibodies in serum. Please refer to Example 4 for details.

Figure 6:
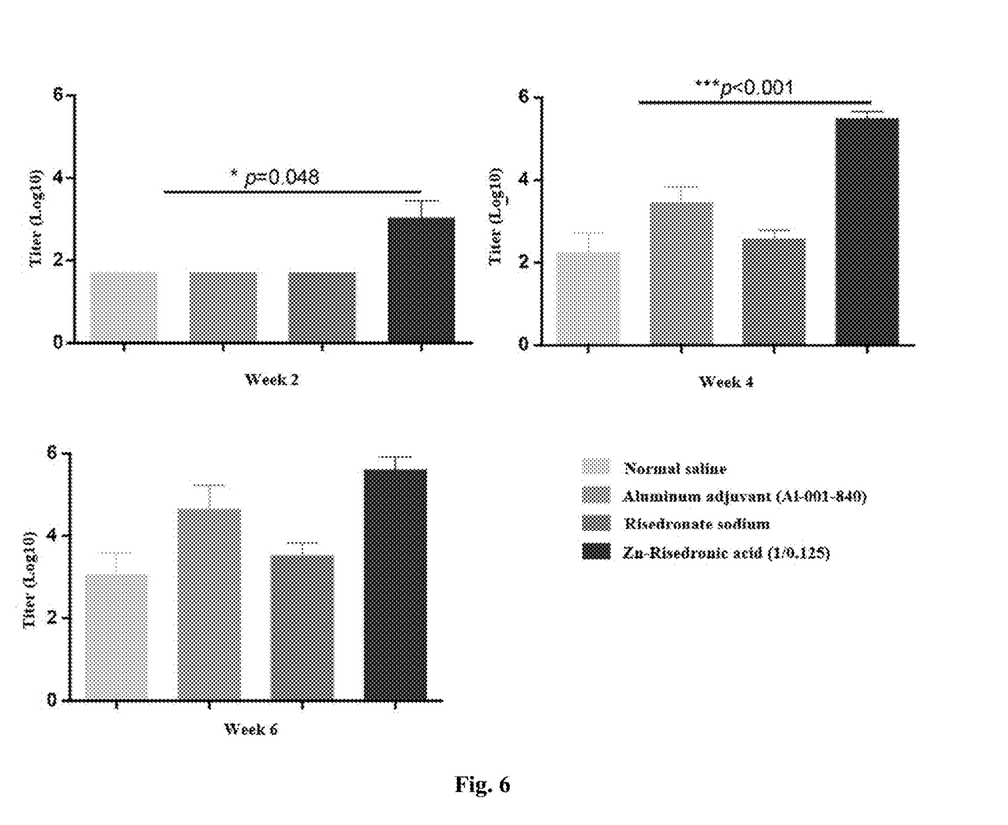
FIG. 6: determination of adjuvant activities of sodium risedronate adjuvant and zinc risedronate adjuvant combined with hepatitis B therapeutic protein, mean±SD: n=5, *p<0.05; p<0.01; *p<0.001, ****p<0.0001.

Experimental results: as shown in FIG. 6, compared with the aluminum adjuvant group, the zinc risedronate adjuvant group was featured with quick and strong onset after one injection of immunization in mice, and the difference was statistically significant; after 3 injections of immunization, that was, at the $4^{th}$ week, its humoral immune response enhancement advantage was still significant compared with the aluminum adjuvant group; after 5 injections of immunization, it was slightly better than that of the aluminum adjuvant group, while sodium risedronate itself also had a certain humoral immune stimulation effect, and showed no statistically significant difference compared with aluminum adjuvant.

Example 7: Study on Dose-Effect Relationship of Zinc Risedronate Adjuvant Activity Using the experimental procedure described in Example 4, mice were immunized with zinc risedronate adjuvant in combination with hepatitis B therapeutic protein by intramuscular injection, and serum antibody titers were detected. The specific method was as follows:

Experimental animals: Balb/C mice, 6-8 weeks, 5 mice/group, female.

Experimental grouping 1: (1) aluminum adjuvant group (Al-001-840); (2) 2× Zn-risedronic acid (1/0.125) group; (3) 0.75× Zn-risedronic acid (1/0.125) group; (4) 0.35× Zn-risedronic acid (1/0.125) group.

Experimental grouping 2: (1) aluminum adjuvant group (Al-001-840); (2) 2× Zn-risedronic acid (1/0.125) group; (3) 1× Zn-risedronic acid (1/0.125) group.

Immunization protocol: antigen 1.2 μg/mouse, adjuvant and hepatitis B therapeutic protein were mixed to form a vaccine at a volume ratio of 1:1, and then injected intramuscularly to mice, 100 μL per mouse, 50 μL on each hind leg. The immunization was performed on the $0^{th}$, $2^{nd}$ and $4^{th}$ week, blood samples were collected from eye socket at the $0^{th}$, $2^{nd}$, $3^{rd}$, $4^{th}$, $5^{th}$ and $6^{th}$ week, and ELISA was used to determine the levels of specific antibodies in serum. Please refer to Example 4 for details.

Figure 7:
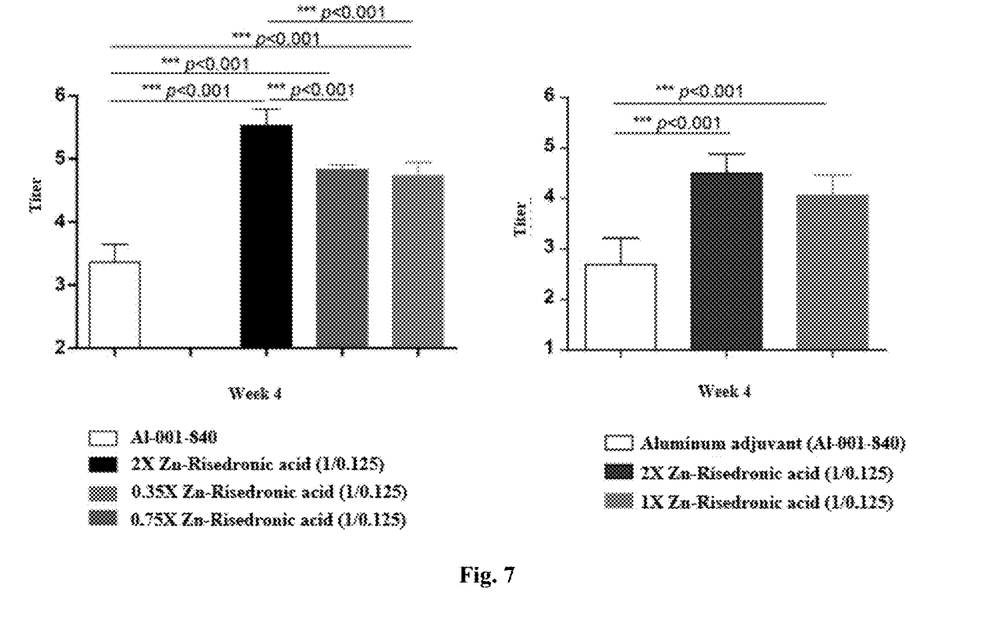
FIG. 7: study on dose-effect relationship of zinc risedronate adjuvant activity, mean±SD: n=5, *p<0.05; p<0.01; *p<0.001, ****p<0.0001.

Experimental results: as shown in FIG. 7, compared the serum antibody titers 2 weeks after 2 injections of immunization, it was found that when Zn-risedronic acid (1/0.125) decreased from 2× (2× was the concentration of adjuvant in the vaccine formulation) to 0.75× and 0.35×, its humoral immune enhancement level and amount of adjuvant used showed a significant dose-effect relationship; meanwhile, when Zn-risedronic acid (1/0.125) decreased from 2× to 1×, its humoral immune response enhancement level showed no statistically significant difference. Taking all the data into consideration, it is confirmed that Zn-risedronic acid (1/0.125) had a significant humoral immune enhancement effect and could be used as an immune enhancer in vaccines in the future.

What is claimed is:

1. A vaccination method for treatment or prevention of infection in a mammal, said method comprising administering a vaccine composition intramuscularly to a mammal, wherein said vaccine composition comprises an antigen and an adjuvant, the adjuvant comprising zinc risedronate micro/nanoparticles, wherein the zinc risedronate micro/nanoparticles consist of zinc and risedronic acid and, optionally phosphate, and wherein the zinc risedronate micro/nanoparticles have a molar concentration ratio of zinc: risedronic acid of 1-8:1.

2. The vaccination method according to claim 1, wherein said zinc risedronate micro/nanoparticles have a molar concentration ratio of zinc: risedronic acid selected from 1:1, 4:1 and 8:1.

3. The vaccination method according to claim 1, characterized in any one of the following:
   (1) said zinc risedronate micro/nanoparticles consist of a phosphate at a molar concentration ratio of zinc: phosphate of 1-8:1; and
   (2) said zinc risedronate micro/nanoparticles consist of a phosphate at a molar concentration ratio of zinc: phosphate selected from 1.5:1 and 4:1.

4. The vaccination method according to claim 1, wherein the zinc risedronate micro/nanoparticles are prepared by a method comprising the following steps:
   a) providing a soluble salt solution containing zinc ions;
   b) evenly mixing the soluble salt solution of step a) with a risedronic acid and a sodium hydroxide; or
      evenly mixing the soluble salt solution of step a) with a risedronic acid, a sodium hydroxide, and a sodium phosphate solution,
   in a manner of sequential precipitation, separated precipitation followed by mixing, or co-precipitation, to obtain the adjuvant comprising zinc risedronate micro/nanoparticles.

5. The vaccination method according to claim 4, characterized in one or more of the following:
   (1) said soluble salt solution comprises a solution of hydrochloric acid; and
   (2) said method further comprises subjecting the mixture of step b) to sterilization, and storing at 2° C. to 8° C. for later use.

6. The vaccination method according to claim 5, characterized in any one of the following:
   (1) said sterilization comprises a sterilization using a high temperature and high pressure sterilization technique; and
   (2) said sterilization comprises a sterilization performed at 121° C. for 30 to 60 minutes.

7. The vaccination method according to claim 1, characterized in one or more of the following:
   (1) said adjuvant has a pH of 8.0-9.0 before sterilization;
   (2) said adjuvant has a pH of 6.0-8.0 after sterilization;
   (3) said zinc risedronate micro/nanoparticles have a particle size of 1-10 μm;
   (4) said adjuvant has a particle zero charge point of 4.0-11.4; and
   (5) said adjuvant has a protein adsorption rate of >60%.

8. The vaccination method according to claim 7, wherein said protein comprises bovine serum albumin.

* * * * *